United States Patent [19]
Dubois

[11] Patent Number: 6,162,444
[45] Date of Patent: Dec. 19, 2000

[54] COSMETIC OR PHARMACEUTICAL COMPOSITIONS

[75] Inventor: Jean-Luc Dubois, Paris, France

[73] Assignee: Hoechst Marion Roussel, France

[21] Appl. No.: 08/383,912

[22] Filed: Feb. 6, 1995

[30] Foreign Application Priority Data

Feb. 16, 1994 [FR] France .................................. 94 01755

[51] Int. Cl.⁷ .................................................. A61K 9/127
[52] U.S. Cl. ............................................ 424/401; 424/450
[58] Field of Search ..................... 424/450, 401

[56] References Cited

U.S. PATENT DOCUMENTS

| | | | |
|---|---|---|---|
| 5,204,105 | 4/1993 | Mausner ................................ | 424/401 |
| 5,358,752 | 10/1994 | Evans et al. ............................ | 424/450 |
| 5,411,981 | 5/1995 | Gaillard-Kelley ...................... | 514/386 |

FOREIGN PATENT DOCUMENTS

| | | |
|---|---|---|
| 0494819 | 7/1992 | European Pat. Off. . |
| 0560138 | 9/1993 | European Pat. Off. . |
| 0580459 | 1/1994 | European Pat. Off. . |
| 2627385 | 8/1989 | France . |
| 4038075 | 3/1992 | Germany . |

OTHER PUBLICATIONS

French Search Report No. 9401755 —T. Steroid Biochem. Molec. vol. 48, No. 1, pp 55–60, 1994, T. Battmann, et al., RU 58841, A New Specific Topical. . . Alopecia and Hirsuti Sm*.

*Primary Examiner*—Thurman K. Page
*Attorney, Agent, or Firm*—Bierman, Muserlian and Lucas

[57] ABSTRACT

A cosmetic or pharmaceutical composition containing a dermatologically effective amount of at least one liposome containing a compound of the formula

I

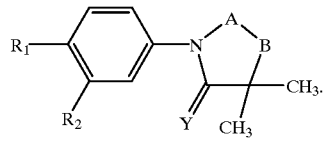

7 Claims, No Drawings

COSMETIC OR PHARMACEUTICAL COMPOSITIONS

STATE OF THE ART

A quite significant number of cosmetic or pharmaceutical preparations containing different active ingredients currently exist on the market. Also, cosmetic and pharmaceutical compositions which contain vesicles of liposome type are known, for example from French patent No. 2,627,385 and EP-A 342,100.

OBJECTS OF THE INVENTION

It is an object of the invention to provide novel cosmetic and dermatological compositions containing at least one liposome containing a compound of formula I and a process for their preparation.

This and other objects and advantages of the invention will become obvious from the following detailed description.

THE INVENTION

The cosmetic and pharmaceutical compositions of the invention contain a dermatologically effective amount of at least one liposome containing a compound of the formula

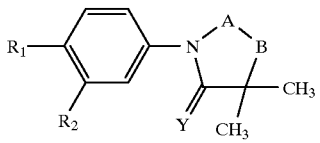

wherein $R_1$ is selected from the group consisting of —CN, —$NO_2$ and halogen, $R_2$ is —$CF_3$ or halogen, -A-B- is selected from the group consisting of

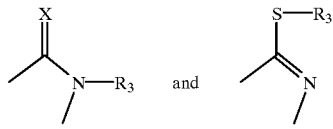

X is oxygen or sulfur, $R_3$ is selected from the group consisting of a) hydrogen, b) alkyl, alkenyl, alkynyl, aryl and aralkyl of up to 12 carbon atoms optionally substituted by at least one member of the group consisting of —OH, halogen —SH, —CN, acyl and acyloxy of up to 7 carbon atoms and aryl, aryloxy, aralkoxy and optionally oxidizied —S—aryl of up to 12 carbon atoms with the aryl and aralkyl optionally substituted with at least one member of the group consisting of halogen, —$CF_3$ and alkyl, alkenyl, alkynyl, alkoxy, alkenyloxy and alkynyloxy of up to 6 carbon atoms, the alkyl, alkenyl and alkynyl being optionally interrupted by at least one oxygen, nitrogen and optionally oxidized sulfur, c) free, amidified and salified carboxy and carboxy esterified with alkyl of 1 to 6 carbon atoms, —$NH_2$, mono and dialkyl amino of 1 to 4 alkyl carbon atoms and a heterocycle of 3 to 6 ring members having at least one heteroatom selected from the group consisting of oxygen, nitrogen and optionally oxidizied sulfur d) trialkylsilyl with alkyl of 1 to 6 carbon atoms and e) acyl and acyloxy of an organic carboxylic acid of up to 7 carbon atoms and Y is selected from the group consisting of oxygen, sulfur and =NH.

The active compounds have been described for example in European Patent Application EP-A No. 494,819 as well as European Patent Application EP-A No. 0,580,459.

The cosmetic or pharmaceutical compositions preferably contain a product of formula I wherein X and Y are oxygen, $R_2$ is halogen or trifluoromethyl, $R_1$ is nitro, halogen or cyano and $R_3$ is hydrogen or alkyl of 1 to 4 carbon atoms optionally substituted by hydroxy or methoxy. Most preferred is the compound of the formula

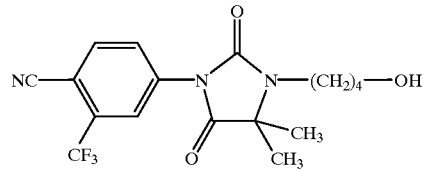

Examples of alkyl of up to 12 carbon atoms are methyl, ethyl, propyl, isopropyl, butyl, isobutyl, sec-butyl, tert-butyl, pentyl, isopentyl, sec-pentyl, tert-pentyl, neo-pentyl, hexyl, isohexyl, sec-hexyl, tert-hexyl, heptyl, octyl, nonyl, decyl, undecyl and dodecyl.

Alkyl of 1 to 6 carbon atoms are preferred and particularly methyl, ethyl, propyl, isopropyl, n-butyl, isobutyl, terbutyl, linear or branched pentyl and linear or branched hexyl.

Examples of alkenyl of up to 12, preferably 4 carbon atoms, are vinyl, allyl, 1-propenyl, butenyl, pentenyl and hexenyl. Among the preferred alkenyl are allyl or butenyl.

Examples of alkynyl of up to 12 and preferably 4 carbon atoms are ethynyl, propargyl, butynyl, pentynyl or hexynyl, most preferably propargyl.

Examples of aryl are carbocyclic aryls such as phenyl or naphthyl or heterocyclic aryls with 5 or 6 ring members containing one or more heteroatoms preferably chosen from oxygen, sulfur and nitrogen. Examples of heterocyclic aryls with 5 members are furyl, thienyl, pyrrolyl, thiazolyl, oxazolyl, imidazolyl, thiadiazolyl, pyrazolyl and isoxazolyl. Examples of heterocyclic aryls with 6 members are pyridyl, pyrimidinyl, pyridazinyl and pyrazinyl. Examples of condensed aryls are indolyl, benzofurannyl, benzothienyl and quinolinyl, phenyl is preferred.

Examples of arylalkyl are alkyls mentioned previously, optionally substituted, and the aryls also mentioned above optionally substituted. Benzyl, phenethyl and triphenylmethyl are preferred.

Examples of halogen includes fluorine, chlorine, bromine or iodine with fluorine, chlorine or bromine being preferred. Examples of alkyl substituted by at least one halogen are monofluoromethyl, chloromethyl, bromomethyl or iodomethyl, difluoromethyl, dichloromethyl or dibromomethyl and trifluoromethyl.

Examples of substituted aryls or arylalkyls are those in which phenyl is substituted by fluorine or by methoxy or trifluoromethyl.

Examples of acyls of organic carboxylic acids of up to 7 carbon atoms are formyl, acetyl, propionyl, butyryl or benzoyl, but it can also be valeryl, hexanoyl, acryloyl, crotonoyl or carbamoyl. Examples of acyloxys are acyls having the meaning above and for example acetyloxy or propionyloxy.

Examples of esterified carboxy are the alkoxycarbonyls such as methoxycarbonyl, ethoxycarbonyl, propoxycarbonyl, butyl or tertbutyloxycarbonyl, cyclobutyloxycarbonyl, cyclopentyloxycarbonyl and cyclohexyloxycarbonyl.

Examples of easily cleavable ester remainders are methoxymethyl, ethoxymethyl; acyloxyalkyl such as pivaloyloxymethyl, pivaloyloxyethyl, acetoxymethyl or acetoxyethyl; alkoxycarbonyloxy alkyl such as methoxycarbonyloxymethyl or ethyl and isopropyloxycarbonyloxy methyl or ethyl. A list of such ester radicals can be found in European Patent EP No. 0,034,536.

Examples of amidified carboxy are

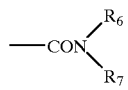

in which $R_6$ and $R_7$ are individually hydrogen or alkyl of 1 to 4 carbon atoms such as methyl, ethyl, propyl, isopropyl, butyl, isobutyl, sec-butyl or tert-butyl.

Among

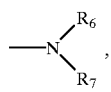

the amino, mono or dimethylamino are preferred.

can also be a heterocycle which may contain an additional heteroatom. Examples thereof include pyrrolyl, imidazolyl, pyridyl, pyrazinyl, pyrimidyl, indolyl, piperidino, morpholino and piperazinyl with piperidino or morpholino being preferred.

Examples of salified carboxy are the salts formed for example with an equivalent of sodium, potassium, lithium, calcium, magnesium or ammonium. There can also be mentioned the salts formed with organic bases such as methylamine, propylamine, trimethylamine, diethylamine, triethylamine. The sodium salt is preferred.

Examples of alkylamino are methylamino, ethylamino, propylamino or butylamino. The alkyls of 1 to 4 carbon atoms are preferred, with the alkyl being chosen from the alkyls mentioned above. Examples of dialkylamino are dimethylamino, diethylamino and methylethylamino with the alkyls having at most 4 carbon atoms chosen from the above-indicated list being preferred.

Examples of heterocyclics containing one or more heteroatoms are the saturated heterocyclic monocyclics such as oxirannyl, oxolannyl, dioxolannyl, imidazolidinyl, pyrazolidinyl, piperidyl, piperazinyl or morpholinyl.

Examples of alkyl, alkenyl or alkynyl optionally interrupted by a heteroatom chosen from sulfur, oxygen or nitrogen are groups containing within their structure one or more of these atoms, these heteroatoms obviously not being able to be situated at the end of the group. Examples include alkoxyalkyl such as methoxymethyl, methoxyethyl, methoxypropyl and methoxybutyl or alkoxyalkoxyalkyl such as methoxyethoxymethyl.

Examples of trialkylsilyls in which the alkyl contains 1 to 6 carbon atoms are trimethylsilyl, triethylsilyl, (1,1-dimethylethyl) dimethylsilyl.

When the products of formula I contain an amino which can be salified by an acid, it is understood that these non-toxic, pharmaceutically acceptable acid addition salts can also be used such as salts formed with hydrochloric acid or methanesulfonic acid.

The preparation process for the products of formula I as defined above is described by EP-A No. 494,819.

The cosmetic or pharmaceutical compositions of the present invention advantageously contain from 0.001 to about 20% by weight, preferably from 0.01 to 10% by weight, of the active compound or compounds of formula I relative to the weight of the total composition. The compositions containing liposomes can be presented in various forms, for example in the form of a gel, cream, milk, balm or lotion.

The active ingredient is at least partly incorporated in vesicles of liposome type, particularly in a proportion of more than 20%, preferably in a proportion of than 50%, and more especially more than 90%.

In principle, the compositions containing liposomes can be prepared according to the following technique which was described in FR-A No. 2,627,385. The active ingredients are first prepared for example, in the form of an aqueous solution if they are soluble in water.

The vesicles of the liposomes are constituted by a lipid phase containing at least one of the following substances: phospholipids of natural or synthetic origin, phospholipids combined with glycerides, phospholipids combined with glycolipids, cerebrosides, sphingolipids, cephalins, phosphoaminolipids, cerebroglucosides and gangliosides, optionally combined with natural or synthetic cholesterol.

This lipid phase is dissolved in a volatile solvent, which varies according to the type of substance chosen, for example an organic solvent such as chloroform or methanol. The lipid solution is placed in a flask and then evaporated under reduced pressure in a rotary evaporator until a film is formed on the walls of the flask. Then, the aqueous solution of the active ingredients to be encapsulated is added under constant stirring to obtain a suspension which is then subjected to ultrasound. Thus, a suspension of liposome-type vesicles is obtained incorporating at least in part the active ingredient in aqueous solution. The encapsulation of the active ingredients thus achieved involves optimizing their cosmetodynamic activity.

The topical use of an active ingredient encapsulated in liposomes allows the active ingredient to be concentrated in the sebaceous glands to obtain a higher and longer-lasting concentration in the epidermis and in the dermis in vivo, than that obtained by standard topical applications. Moreover, the systemic effect is limited by minimizing the passage of the active ingredient into the blood circulation and the side effects of the products are therefore reduced.

The percutaneous penetration of the active ingredient therefore depends on the active compound and the method by which the liposomes are produced.

The preparation of the compositions containing liposomes using the lipid phase dissolved in a volatile solvent has disadvantages because traces of solvent can still be found in the final composition. Also, an object of the invention is a method for preparing liposomes which does not use organic solvents and which produces satisfactory results as far as percutaneous penetration of the active ingredient is concerned.

The invention relates to a preparation process for a cosmetic or pharmaceutical composition consisting of liposomes comprising preparing an emulsion or aqueous suspension containing an active compound (for example, a compound of formula I) and at least one lipid compound and optionally additives such as a pH buffer, an anti-oxidant or an antiseptic, and stirring the emulsion or the suspension at a temperature of 40° to 80° C., preferably 40° to 75° C., especially 60° to 70° C., and then reducing the size of the liposomes. Preferably, a solid dispersion containing the active compound, one or more lipid compounds and optionally additives is prepared hot, and this solid dispersion is placed in water. This process is carried out without using organic solvents.

In a preferred mode of the process, a mixture of lipidic constituents comprising one or more active principles, the phospholipids and the preservatives is prepared beforehand, which is then heated at a temperature comprised of 40° to 80° C. up to melting and then the mixture is stirred in the presence of the hydrophilic compounds comprising the pH buffer, one or more antiseptics to obtain the solution of liposomes which is submitted to a process of size reduction.

The originality of the invention also resides in the fact that the active ingredient has a low melting point of about 100° C. and that this active ingredient is dissolved in or is soluble in the phospholipid or the phospholipid mixture at low temperature (for example between 50° and 70° C.). Moreover, this low temperature minimizes the oxidation or the degradation of the phospholipids and corresponds to the optimal temperature for emulsification of the phospholipids in water or in the pH buffer.

The process of the invention can be carried out with various active ingredients but preferably the compound of formula I has the formula

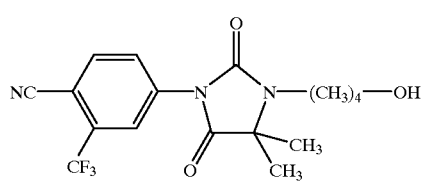

Very useful compositions are obtained by using the method described.

Examples of lipid compound are a natural, semi-synthetic or synthetic phospholipid, for example Lipoid E 100.35, Lipoid EPC 3 or Lipoid SPC 3, hydrogenated or not (which are marketed by the Société Diététique Française de Formulation et de Frabrication, 24, Avenue Hoche, 75008 Paris, France). The three products have a molecular weight between 777 and 790, a transition temperature between 45° and 60° C. and consist of more than 90% of egg phosphatidylcholine or soya phosphatidylcholine.

Examples of pH buffers are a phosphate buffer of pH 7. Examples of anti-oxidants are α-tocopherol acetate or α-tocopherol used for example, at a concentration comprised between 0.1 and 5%, preferably between 0.5 and 2% of the weight of the lipid compounds. Examples of antiseptics are generally known compounds such as p-hydroxybenzoates of propyl, ethyl or methyl at a concentration of 0.01 to 0.5% and preferably between 0.05 and 0.1%, or also Bronopol at a concentration of 0.1%.

For the preparation of medicaments, other additives can also be added to the described compositions. For example, for the preparation of the gel, carboxymethylcellulose (Blanose®) or another commonly-used gelling agent is added slowly to the liposome suspension with stirring at ambient temperature to obtain gels with 0.5%, 0.75%, 1% and 1.25% of Blanose®.

According to the process described, a molar ratio of phospholipid/active ingredient of formula I of between 1.0 and 20.0, preferably between 5.5 and, 15.0, especially between 8 and 12 for the compound of formula I' as active ingredient, is normally used. The percentage of encapsulation of the active compound normally increases with the molar ratio of lipid/active compound.

The concentration of active ingredient in the aqueous suspension depends on the concentration of phospholipids. Normally, a concentration of more than 10 mmol of phospholipids per liter of aqueous phase is used, preferably between 30 and 400 mmol/l, most preferably between 60 and 300 mmol/l.

In principle, various known methods for reducing the size of the liposomes are applicable. Preferably, a micro-fluidizer is used (see Vemuri et al., "Large-scale Production of Liposomes by a Micro-fluidizer", Drug Develop. Ind. Pharm.; 1990; 16,15; 2243–2256). In the interaction chamber of the micro-fluidizer, two flows of the liposome suspension enter into collision at high pressure and at great speed. The result is a reduction in the size of the vesicles.

The temperature during the fusion, emulsification and passage into the micro-fluidizer must normally be greater than the transition temperature of the lipid compounds. Preferably, the process of the invention is characterized in that the emulsion or the suspension is stirred at a temperature comprised between 40° and 75° C.

The liposomes obtained using the micro-fluidizer have sizes which are identical to or smaller than those obtained by the methods using ultrasound (see Mayhew et al., "A practical method for the large scale manufacture of liposomes", Pharmaceutical Manufacturing, 1985, 8, 18–22). The emulsion or the suspension containing the liposomes can pass through the micro-fluidizer once or several times. Normally, they are passed through the micro-fluidizer 1 to 6, preferably 2 to 5, times because after this, no significant changes in the size of the liposomes are observed. The process of the invention is therefore characterized in that at least one pass of the emulsion or the suspension through a micro-fluidizer is used to reduce the size of the liposomes.

The preparation for the cosmetic or pharmaceutical compositions is easy to reproduce and can be carried out on an industrial scale. Moreover, preparations with a high content of phospholipids and active ingredient can be obtained. The pharmaceutical preparations can be used as medicaments for example in dermatology, because there is optimal penetration of the active ingredient through the skin.

According to the invention, the liposomes containing the active ingredient localize the penetration into the epidermis and into the sebaceous glands while minimizing passage into the circulatory system.

The compositions of the invention can also be used as medicaments for the treatment of adenomas and neoplasias of the prostate, for combating benign hypertrophy of the prostate, for the treatment of benign or malignant tumors, the cells of which contain particularly androgen receptors. There can particularly be mentioned mainly cancers of the breast, the skin and the ovaries but also cancers of the bladder, the lymphatic system, the kidney, the liver. Moreover, the compositions can also be used in the treatment of hirsutism, acne, seborrhea, androgenic alopecia, hyperpilosity and in cosmetology.

The compositions can therefore be used in dermatology, either alone or in combination. They can be combined particularly with an antibiotic product such as a derivative of azelaic or fusidic acid, erythromycin or with a derivative of the retinoids for the treatment of acne, or with a 5α-reductase inhibitor such as (5α, 17β)-1,1-dimethylethyl-3-oxo-4-aza-Δ¹-androstene-17-carboxamide (or Finasteride, Merck, 11th Ed.) or azelaic acid or a blocking agent of the androgen receptors for the treatment of acne, alopecia or hirsutism, or with a product stimulating hair growth such as Minoxidil for the treatment of alopecia.

The compositions can also be used in the veterinary domain. The compositions containing radioactive products can also be used in diagnostics as specific markers of the androgen receptors. As radioactive products, there can be used, for example, active ingredients marked with tritium, with carbon 14 or also with iodine 125.

In the following examples, there are described several preferred embodiments to illustrate the invention. However, it is to be understood that the invention is not intended to be limited to the specific embodiments.

EXAMPLE 1

Preparation of 4-(4,4-dimethyl-2,5-dioxo-3-(4-hydroxy-butyl)-1-imidazolidinyl)-2-(trifluoromethyl)-benzonitrile a) Condensation 600 mg of 4-(4,4-dimethyl-2,5-dioxo-1-imidazolidinyl)-2-(trifluoromethyl)-benzonitrile obtained as in Example 8 of European Patent Application No. 0,494,819 in 5 ml of dimethylformamide were added to a suspension of 104 mg of sodium hydride in 0.8 ml of dimethylformamide while maintaining the temperature below 20° C. After stirring for 10 minutes, 445 mg of 4-chloro-t-butyl-dimethyl-silyl ether and 300 mg of sodium iodide were added. The mixture was heated for 16 hours at 50° C., cooled to ambient temperature and 87 mg of sodium hydride and then a further 400 mg of chlorinated ether and 267 mg of sodium hydride were added. Heating was continued for another hour and then the reaction medium was returned to ambient temperature and poured into 60 ml of water containing 600 mg of monopotassium phosphate. Extraction was carried out with ether and the organic phase was washed with water, dried and the solvent was evaporated. The residue was chromatographed on silica (eluant: methylene chloride-acetone (99–1)) to obtain 526 mg of the expected product which was used as is for the following stage.

b) Cleavage

The product of Step a) was mixed with 5 ml of methanol and 1.5 ml of 2N hydrochloric acid and the mixture was stirred for 40 minutes at ambient temperature, poured into 30 ml of water and extracted with methylene chloride. The organic phase was washed with water, dried and the solvent was evaporated. After chromatographing the residue on silica (eluant: methylene chloride-acetone (9–1)), the fractions with $R_f$=0.15 were collected and crystallized from isopropyl ether to obtain 307 mg of the expected product melting at 102–103° C.

Preparation of the 4-chloro-1-butyl-dimethylsilyl ether.

9.9 ml of 4-chloro-1-butanol and 24.3 g of imidazole were stirred in 50 ml of tetrahydrofuran. 2.82 g of terbutyldimethylsilyl chloride in 20 ml of tetrahydrofuran were added dropwise at a temperature below 20° C. The mixture was stirred for 18 hours at ambient temperature, followed by separating, rinsing with tetrahydrofuran and the solvent was eliminated under reduced pressure. The residue was purified by chromatography on silica (eluant: cyclohexane-ethyl acetate (95–5)) to obtain 17.5 g of the expected product.

EXAMPLE 2

The following active ingredients are described and prepared as indicated in European Patent Applications EP-A 494,819 and EP-A 0,580,459:

(1,1-dimethyl)-ethyl 3-(4-cyano-3-(trifluoromethyl)-phenyl-5,5-dimethyl-2,4-dioxo-1-imidazolidine-acetate, cyclopentyl 3-(4-cyano-3-(trifluoromethyl)-phenyl)-5,5-dimethyl- 2,4-dioxo-1-imidazolidine-acetate, ethyl 3-(4-cyano-3-(trifluoromethyl)-phenyl)-5,5-dimethyl-2,4-dioxo-1-imidazolidine-butanoate, 3-(4-cyano-3-(trifluoromethyl)-phenyl)-5,5-dimethyl-2,4-dioxo-1-imidazolidine-butanoic acid, (1,1-dimethyl)-ethyl 3-(4-cyano-3-(trifluoromethyl)-phenyl)-5,5-dimethyl-2,4-dioxo-1-imidazolidine-butanoate, cyclopentyl 3-(4-cyano-3-(trifluoromethyl)-phenyl)-5,5-dimethyl- 2,4-dioxo-1-imidazolidine-butanoate, 4-(4,4-dimethyl-2,5-dioxo-3-(2-((4-fluorophenyl)-thio)-ethyl)-1-imidazolidinyl-2-(trifluoromethyl)-benzonitrile, 4-(4,4-dimethyl-2,5-dioxo-3-(2-((4-fluorophenyl)-sulfonyl)-ethyl) -1-imidazolidinyl-2-(trifluoromethyl)-benzonitrile, 4-(4,4-dimethyl-2,5-dioxo-3-(2-((4-fluorophenyl)-sulfinyl)-ethyl)-1-imidazolidinyl-2-(trifluoromethyl)-benzonitrile, 4-(4,4-dimethyl-2,5-dioxo-3-((3-methoxyphenyl)-methyl)-1-imidazolidinyl-2-(trifluoromethyl)-benzonitrile, 4-(4,4-dimethyl-2,5-dioxo-3-(2-(4-morpholinyl)-ethyl)-1-imidazolidinyl-2-(trifluoromethyl)-benzonitrile, 4-(4,4-dimethyl-3-(2-hydroxyethyl)-5-imino-2-thioxo-1-imidazolidinyl)-2-(trifluoromethyl)-benzonitrile, 4-(4,4-dimethyl-3-(2-hydroxyethyl)-5-oxo-2-thioxo-1-imidazolidinyl)-2-(trifluoromethyl)-benzonitrile, 4-(4,4-dimethyl-3-(2-hydroxyethyl)-5-imino-2-thioxo-1-imidazolidinyl)-2-(trifluoromethyl)-5-$^3$H-benzonitrile, 4-(4,4-dimethyl-3-(2-hydroxyethyl)-5-oxo-2-thioxo-1-imidazolidinyl)-2-(trifluoromethyl)-5-$^3$H-benzonitrile, 4-(4,4-dimethyl-3-(3-hydroxypropyl)-5-imino-2-thioxo-1-imidazolidinyl)-2-(trifluoromethyl)-benzonitrile, 4-(4,4-dimethyl-3-(3-hydroxypropyl)-5-oxo-2-thioxo-1-imidazolidinyl)-2-(trifluoroethyl)-benzonitrile, 4-(4,4-dimethyl-3-(4-hydroxybutyl)-5-imino-2-thioxo-1-imidazolidinyl)-2-(trifluoromethyl)-benzonitrile, 4-(4,4-dimethyl-3-(4-hydroxybutyl)-5-oxo-2-thioxo-1-imidazolidinyl)-2-(trifluoromethyl)-benzonitrile, 4-(4,4-dimethyl-3-(2-methoxyethyl)-5-imino-2-thioxo-1-imidazolidinyl)-2-(trifluoromethyl)-benzonitrile, 4-(4,4-dimethyl-3-(2-methoxyethyl)-5-oxo-2-thioxo-1-imidazolidinyl)-2-(trifluoromethyl)-benzonitrile, 4-(4,4-dimethyl-3-(1-methylethyl)-5-imino-2-thioxo-1-imidazolidinyl)-2-(trifluoromethyl)-benzonitrile, 4-(4,4-dimethyl-3-(1-methylethyl)-5-oxo-2-thioxo-1-imidazolidinyl)-2-(trifluoromethyl)-benzonitrile, 3-(3,4-dichlorophenyl-5,5-dimethyl-1-(3-hydroxypropyl)-4-imino-2-imidazolidine-thione, 3-(3,4-dichlorophenyl-5,5-dimethyl-1-(3-hydroxypropyl)-2-thioxo-4-imidazolidinone, 4-(4,4-dimethyl-3-(4-hydroxybutyl)-5-imino-2-thioxo-1-imidazolidinyl)-2-(trifluoromethyl)-(5-$^3$H)-benzonitrile, 4-(4,4-dimethyl-3-(4-hydroxybutyl)-5-oxo-2-thioxo-1-imidazolidinyl)-2-(trifluoromethyl)-(5-$^3$H)-benzonitrile, 4-(4,4-dimethyl-3-(4-hydroxybutyl)-5-imino-2-thioxo-1-imidazolidinyl)-2-(trifluoromethyl)-benzo-($^{14}$C)-nitrile, 4-(4,4-dimethyl-3-(4-hydroxybutyl)-5-oxo-2-thioxo-1-imidazolidinyl)-2-(trifluoromethyl)-benzo-($^{14}$C)-nitrile, 4-(4,4-dimethyl-3-(4-hydroxybutyl)-5-imino-2-oxo-1-imidazolidinyl)-2-(trifluoromethyl)-(5-$^3$H)-benzonitrile, 4-(4,4-dimethyl-2,5-dioxo-3-(4-hydroxybutyl)-1-imidazolidinyl)-2-(trifluoromethyl)-(5-$^3$H)-benzonitrile, 4-(4,4-dimethyl-3-(4-hydroxybutyl)-5-imino-2-oxo-1-imidazolidinyl)-2-(trifluoromethyl)-benzo-($^{14}$C)-nitrile, 4-(4,4-dimethyl-2,5-dioxo-3-(4-hydroxybutyl)-1-imidazolidinyl)-2-(trifluoromethyl)-benzo-($^{14}$C)-nitrile, 4-(2,5-dioxo-4,4-dimethyl-3-(4-triphenylmethoxybutyl)-1-imidazolidinyl)-2-(trifluoromethyl)-benzonitrile, 4-(2,5-dioxo-4,4-dimethyl-3-(4-phenylmethoxybutyl)-1-imidazolidinyl)-2-(trifluoromethyl)-benzonitrile, 4-[4,4-dimethyl-2,5-dioxo-3-(4-methoxybutyl)-1-imidazolidinyl]-2-(trifluoromethyl)-benzonitrile, 4-[3-(4-chlorobutyl)-4,4-dimethyl-2,5-dioxo-1-imidazolidinyl]-2-(trifluoromethyl)-benzonitrile, 4-[3-[4-[(methylsulphonyl)-oxy]-butyl]-4,4-dimethyl-2,5-dioxo-1-imidazolidinyl]-2-(trifluoromethyl)-benzonitrile, 4-(3-acetyl-4,4-dimethyl-2,5-dioxo-1-imidazolidinyl)-2-(trifluoromethyl)-benzonitrile, 4-(3-benzoyl-4,4-dimethyl-2,5-dioxo-1-imidazolidinyl)-2-(trifluoromethyl)-benzonitrile, 4-[3-[dimethyl-(1,1-dimethylethyl)-silyl]-4,4-dimethyl-2,5-dioxo-1-imidazolidinyl]-2-(trifluoromethyl)-benzonitrile, 1-(4-nitro-3-(trifluoromethyl)-phenyl)-3,4,4-trimethyl-2,5-imidazolidinedione, 5,5-dimethyl-1-ethyl-3-(4-nitro-3-(trifluoromethyl)-phenyl)-2,4-imidazolidinedione, 5,5-dimethyl-3-(4-nitro-3-(trifluoromethyl)-phenyl)-1-propyl-2,4-imidazolidinedione, 5,5-dimethyl-1-(1-methyl ethyl)-3-(4-nitro-3-(trifluoromethyl)-phenyl)-2,4-imidazolidinedione, 5,5-dimethyl-3-(4-nitro-3-trifluoromethyl)-phenyl)-1-(2-propenyl)-2,4-imidazolidinedione, 5,5-dimethyl-3-(4-nitro-3-(trifluoromethyl)-phenyl)-1-methyl phenyl-2,4-imidazolidinedione.

4-(4,4-dimethyl-5-imino-2-oxo-1-imidazolidinyl)-2-(trifluoromethyl)-benzonitrile, 4-(4,4-dimethyl-2,5-dioxo-1-imidazolidinyl)-2-(trifluoromethyl)-benzonitrile, 3-(4-cyano-3-(trifluoromethyl)-phenyl)-5,5-dimethyl-2,4-dioxo-1-imidazolidine acetic acid, ethyl 3-(4-cyano-3-(trifluoromethyl)-phenyl)-5,5-dimethyl-2,4-dioxo-1-imidazolidine-acetate, 4-(5-imino-2-thioxo-3,4,4-trimethyl-1-imidazolidinyl)-2-(trifluoromethyl)-benzonitrile, 4-(5-oxo-2-thioxo-3,4,4-trimethyl-1-imidazolidinyl)-2-(trifluoromethyl)-benzonitrile, 4-(2,5-dithioxo-3,4,4-trimethyl-1-imidazolidinyl)-2-(trifluoromethyl)-benzonitrile, 4-(4,4-dimethyl-5-imino-2-thioxo-1-imidazolidinyl)-2-(trifluoromethyl)-benzonitrile, 4-(4,4-dimethyl-5-oxo-2-thioxo-1-imidazolidinyl)-2-(trifluoromethyl)-benzonitrile, 5,5-dimethyl-3-(4-nitro-3-(trifluoromethyl)-phenyl)-1-pentyl-2,4-imidazolidinedione, 5,5-dimethyl-3-(4-nitro-3-(trifluoromethyl)-phenyl)-1-nonyl-2,4-imidazolidinedione, 4-(3,4,4-trimethyl-2,5-dioxo-1-imidazolidinyl)-2-(trifluoromethyl)-benzonitrile, 4-(5-thioxo-2-oxo-3,4,4-trimethyl-1-imidazolidinyl)-2-(trifluoromethyl)-benzonitrile (product A), 4-(5-oxo-2-thioxo-3,4,4-trimethyl-1-imidazolidinyl)-2-(trifluoromethyl)-benzonitrile (product B), 4-(2,5-dithioxo-3,4,4-trimethyl-1-imidazolidinyl)-2-(trifluoromethyl)-benzonitrile (product C), 4- (4,5-dihydro-4,4-dimethyl-2-(methylthio)-5-oxo-1H-imidazol-1-yl)-2-(trifluoromethyl)-benzonitrile, 4-[4,5-dihydro-4,4-dimethyl-5-oxo-2-[(phenylmethyl)-thio]-1H-imidazol-1-yl]-2-(trifluoromethyl)-benzonitrile, 4-[4,4-dimethyl 3-(2-hydroxyethyl)-5-imino-2-thioxo-1-imidazolidinyl]-2-(trifluoromethyl)-benzonitrile, 4-[4,4-dimethyl-3-(2-hydroxyethyl)-5-oxo-2-thioxo-1-imidazolidinyl]-2-(trifluoromethyl)-benzonitrile (Product A) and 4-[4,4-dimethyl-2,5-dioxo-3-(2-mercaptoethyl)-1-imidazolidinyl]-2-(trifluoromethyl)-benzonitrile (Product B), 4-(4,4-dimethyl-2,5-dioxo-3-ethyl-1-imidazolidinyl)-2-(trifluoromethyl)-benzonitrile, 4-(4,4-dimethyl-2,5-dioxo-3-(2-propenyl)-1-imidazolidinyl)-2-(trifluoromethyl)-benzonitrile, 4-(4,4-dimethyl-2,5-dioxo-3-(benzyl)-1-imidazolidinyl)-2-(trifluoromethyl)-benzonitrile, 4-[4,4-dimethyl-2,5-dioxo-3-[4-fluorobenzyl]-1-imidazolidinyl]-2-(trifluoromethyl)-benzonitrile, 4-[4,4-dimethyl-2,5-dioxo-3-[4-methoxy-benzyl]-1-imidazolidinyl]-2-(trifluoromethyl)-benzonitrile, 4-[4,4-dimethyl-2,5-dioxo-3-[4-trifluoromethyl)-benzyl]-1-imidazolidinyl]-2-(trifluoromethyl)-benzonitrile, 4-[4,4-dimethyl-2,5-dioxo-3-(2-epoxymethyl)-1-imidazolidinyl]-2-(trifluoromethyl)-benzonitrile, 4-(4,4-dimethyl-2,5-dioxo-3-propyl-1H-imidazolidinyl)-2-(trifluoromethyl)-benzonitrile, 4-(4,4-dimethyl-2,5-dioxo-3-ispropyl-1-imidazolidinyl]-2-(trifluoromethyl)-benzonitrile, 4-[4,5-dihydro-4,4-dimethyl-2-(nonylthio)-5-oxo-1H-imidazol-1-yl] 2-(trifluoromethyl)-benzonitrile, 4-[4,5-dihydro-4,4-dimethyl-2-[(3-hydroxypropyl)-thio]-5-oxo-1H-imidazol-1-yl]-2-(trifluoromethyl)-benzonitrile, ethyl-[[1-[4-cyano-3-(trifluoromethyl)-phenyl]-4,5-dihydro-4,4-dimethyl-5-oxo-1H-imidazol-2-yl] thio]-acetate, 4-(4,4-dimethyl-3-ethyl-5-imino-2-thioxo-1-imidazolidinyl)-2-(trifluoromethyl)-benzonitrile, 4-(4,4-dimethyl-5-imino-3-pentyl-2-thioxo-1-imidazolidinyl)-2-(trifluoromethyl)-benzonitrile, 4-(4,4-dimethyl-3-ethyl-5-oxo-2-thioxo-1-imidazolidinyl)-2-(trifluoromethyl)-benzonitrile, 4-(4,4-dimethyl-5-oxo-3-pentyl-2-thioxo-1-imidazolidinyl)-2-(trifluoromethyl)-benzonitrile, 4-[4,5-dihydro-4,4-dimethyl-2-(methylthio)-5-thioxo-1H-imidazol-1-yl]-2-(trifluoromethyl)-benzonitrile, 4-[4,5-dihydro 4,4-dimethyl-2-[benzyl-thio]-5-thioxo-1H-imidazol-1-yl]-2-(trifluoromethyl)-benzonitrile, 3-[4-cyano-3-(trifluoromethyl)-phenyl]-5,5-dimethyl-2,4-dioxo-N-methyl-N-isopropyl-1-imidazolidine-acetamide, 4,-[4,4-dimethyl-2,5-dioxo-3-(2-hydroxyethyl)-1-imidazolidinyl]- 2-(trifluoromethyl)-benzonitrile, 4-[4,4-dimethyl-2,5-dioxo-3-(3-hydroxypropyl)-1-imidazolidinyl]- 2-(trifluoromethyl)-benzonitrile, 4-[3-[2-(acetyloxy)-ethyl]-4,4-dimethyl-2,5-dioxo-1-imidazolidinyl]-2-(trifluoromethyl)-benzonitrile, 4-[4,4-dimethyl-2,5-dioxo-3-(5-hydroxypentyl)-1-imidazolidinyl]- 2-(trifluoromethyl)-benzonitrile, 4-[4,4-dimethyl-2,5-dioxo-3-(2-methoxyethyl)-1-imidazolidinyl]-2-(trifluoromethyl)-benzonitrile, 4-[4,4-dimethyl-2,5-dioxo-3-(cyanomethyl)-1-imidazolidinyl]-2-(trifluoromethyl)-benzonitrile, 4-[4,4-dimethyl-2,5-dioxo-3-[(1,3-dioxalan-2-yl)-methyl]-1-imidazolidinyl]-2-(trifluoromethyl)-benzonitrile, 4-[4,4-dimethyl-2,5-dioxo-3-(2-chloroethyl)-1-imidazolidinyl]-2-(trifluoromethyl)-benzonitrile, 1-(3,4-dichlorophenyl)-5-imino-3,4,4-trimethyl-2-imidazolidine-thione, 3-(3,4-dichlorophenyl)-2-thioxo-1,5,5-trimethyl-4-imidazolidinone, 3-(3,4-dichlorophenyl)-3,5-dihydro-5,5-dimethyl-2-(methylthio) 4H-imidazol-4-one, 1-(3,4-dichlorophenyl)-3,4,4-trimethyl-2,5-imidazolidine-dithione, 1-[4-chloro-3-(trifluoromethyl)-phenyl]-4,4-dimethyl-2-thioxo-5-imidazolidinone, 1-[4-chloro-3-(trifluoromethyl)-phenyl]-4,4-dimethyl-5-imino-2-imidazolidine-thione and 3-(3,4-dichlorophenyl)-3,5-dihydro-5,5-dimethyl-2-[(phenylmethyl)-thio]-4H-imidazol-4-one.

EXAMPLE 3

A Composition Containing Liposomes 0.13 g of α-tocopherol was added to a mixture of 0.5 g of 4-(4,4-dimethyl-2,5-dioxo-3-(4-hydroxybutyl)-1-imidazolidinyl)-2-(trifluoromethyl)-benzonitrile and 10.77 g of phospholipid (lipoid E.100.35). The mixture was heated with stirring at a temperature greater than the transition temperature of the phospholipid, preferably at 60° C.–70° C. The transition temperature of the phospholipid was preferably about 60° C. A solution was prepared which contained 0.1 g of methyl p-hydroxybenzoate and 0.05 g of propyl p-hydroxybenzoate in 100 ml of pH 7 buffer solution heated to a high temperature (i.e. 100° C.) and the solution was added to the mixture of the active ingredient and phospholipid.

α-tocopherol acetate or α-tocopherol was added to this solution and stirring was carried out until the mixture was homogeneous. This solution was passed through a microfluidizer (1 to 6 passes, pressure 15 to 140 MPa) and the preparation can be used as is or it can be incorporated with a gelling agent such as hydroxypropyl cellulose (Blanose T6F) at the rate of 1% or any other gelling agent. The final composition contained liposomes whose size was between 40 and 120 nm. The composition was useful for the treatment of illnesses and in cosmetology or dermatology.

EXAMPLE 4

Using a preparation similar to that described in Example 3, compositions were prepared consisting of liposomes which contain the active compounds of Example 2.

Various modifications of the compositions and method of the invention may be made without departing from the spirit or scope thereof and it should be understood that the invention is intended to be limited only as defined in the appended claims.

What we claim is:

1. A cosmetic or pharmaceutical composition containing a dermatogically effective amount of at least one liposome containing an active compound of the formula

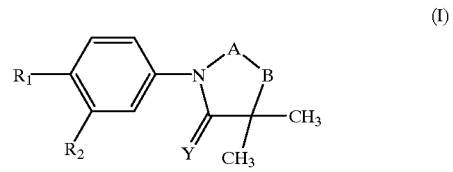

(I)

wherein $R_1$ is selected from the group consisting of —CN, —NO$_2$ and halogen, $R_2$ is —CF$_3$ or halogen, -A-B- is selected from the group consisting of

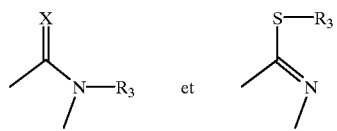

wherein X and Y are oxygen and $R_3$ is selected from the group consisting of hydrogen and alkyl of 1 of 4 carbon atoms optionally substituted with —OH or methoxy and wherein the costmetic or pharmaceutical compositon is free of volatile solvents.

2. A composition of claim 1 wherein the active compound has the formula

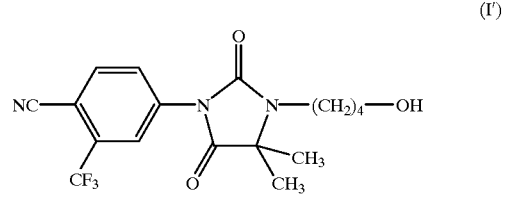

(I')

3. A process for the preparation of an organic solvent-free cosmetic or pharmaceutical composition containing a dermatologically effective amount of at least one liposome containing an active compound of the formula

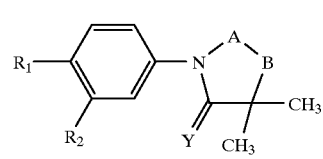

I wherein $R_1$ is selected from the group consisting of —CN, —$NO_2$ and halogen, $R_2$ is —$CF_3$ or halogen, -A-B- is selected from the group consisting of

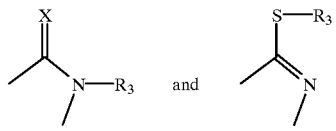

X is oxygen or sulfur, $R_3$ is selected from the group consisting of a) hydrogen, b) alkyl, alkenyl, alkynyl, aryl and aralkyl of up to 12 carbon atoms optionally substituted by at least one member of the group consisting of —OH, halogen —SH, —CN, acyl and acyloxy of up to 7 carbon atoms and aryl, aryloxy, aralkoxy and optionally oxidized —S—aryl of up to 12 carbon atoms with the aryl and aralkyl optionally substituted with at least one member of the group consisting of halogen, —$CF_3$ and alkyl, alkenyl, alkynyl, alkoxy, alkenyloxy and alkynyloxy of up to 6 carbon atoms, the alkyl, alkenyl and alkynyl being optionally interrupted by at least one oxygen, nitrogen and optionally oxidized sulfur, c) free, amidified and salified carboxy and carboxy esterified with alkyl of 1 to 6 carbon atoms, —$NH_2$, mono and dialkyl amino of 1 to 4 alkyl carbon atoms and a heterocycle of 3 to 6 ring members having at least one heteroatom selected from the group consisting of oxygen, nitrogen and optionally oxidized sulfur d) trialkyl-silyl with alkyl of 1 to 6 carbon atoms and e) acyl and acyloxy of an organic carboxylic acid of up to 7 carbon atoms and Y is selected from the group consisting of oxygen, sulfur and =NH consisting essentially of a) forming an aqueous emulsion or suspension of a solid dispersion of a compound of formula I in at least one liposome in the absence of organic solvents, b) stirring the emulsion or suspension at a temperature of 40 to 80° C. and c) reducing the size of liposomes.

4. A method of treating the skin of warm-blooded animals comprising topically applying to the skin of warm-blooded animals a composition of claim 1.

5. The process of claim 4 wherein the compound in the liposome has the formula

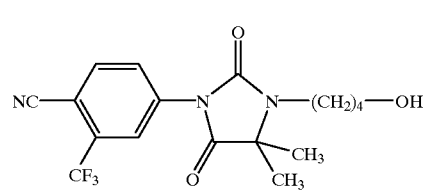

I'

6. The process of claim 4 wherein the lipid is a phospholipid.

7. The process of claim 4 wherein the emulsion or suspension is stirred at 40° to 75° C. and subjected to at least one pass through a microfilter to reduce the size of the liposomes.

* * * * *